United States Patent [19]

Mitchell

[11] Patent Number: 4,919,955
[45] Date of Patent: Apr. 24, 1990

[54] METHOD FOR PACKAGING PERISHABLE PRODUCTS

[76] Inventor: Jerry L. Mitchell, P.O. Box 667, Livingston, Tex. 77351

[21] Appl. No.: 214,195

[22] Filed: Jun. 27, 1988

Related U.S. Application Data

[62] Division of Ser. No. 94,384, Sep. 8, 1987, abandoned.

[51] Int. Cl.$^5$ .............................................. B65B 31/04
[52] U.S. Cl. .................................. 426/394; 426/263; 426/396; 426/404; 426/418; 426/112; 426/129; 426/316; 206/213.1; 53/432
[58] Field of Search ............... 426/112, 118, 418, 419, 426/129, 316, 324, 396, 404, 263, 394; 53/432-434; 215/247; 206/213.1, 524.8

[56] References Cited

U.S. PATENT DOCUMENTS

| | | | |
|---|---|---|---|
| 30,045 | 7/1879 | Greene | 206/455 |
| 1,207,814 | 12/1916 | Stockton. | |
| 1,509,916 | 9/1924 | Waite | 53/432 |
| 2,161,071 | 6/1939 | McGrath et al. | 99/171 |
| 2,316,607 | 4/1943 | MacDonald | 119/2 |
| 2,364,126 | 12/1944 | Cantor et al. | 215/247 |
| 2,402,199 | 6/1946 | MacDonald | 99/188 |
| 2,506,769 | 5/1950 | Bergstein | 53/432 |
| 2,638,263 | 5/1953 | Jesnig | 426/118 |
| 2,709,519 | 5/1955 | Cushman | 53/432 |
| 2,814,382 | 11/1957 | Lassiter | 206/46 |
| 2,847,313 | 8/1958 | Ellies et al. | 99/174 |
| 2,863,267 | 12/1958 | Moore | 53/434 |
| 3,047,404 | 7/1962 | Vaughan | 426/129 |
| 3,286,430 | 2/1963 | Esty | 53/21 |
| 3,348,358 | 10/1967 | Sternau | 426/396 |
| 3,360,382 | 12/1965 | Miller | 99/174 |
| 3,445,240 | 5/1969 | Bedrosian et al. | 426/418 |
| 3,574,642 | 4/1971 | Weinke | 99/174 |
| 3,610,516 | 10/1971 | Joseph | 229/53 |
| 3,625,713 | 12/1971 | Mixon | 99/194 |
| 3,659,393 | 5/1972 | Richter | 53/433 |
| 3,673,758 | 7/1972 | Esty | 53/22 B |
| 3,673,760 | 7/1972 | Canamero et al. | 53/433 |
| 3,715,860 | 2/1973 | Esty | 53/22 B |
| 3,799,427 | 3/1974 | Goglio. | |
| 3,804,962 | 4/1974 | Pipkins | 426/418 |
| 3,851,080 | 11/1974 | Lugg et al. | 426/312 |
| 3,851,437 | 12/1974 | Waldrop et al. | 53/22 B |
| 3,930,040 | 12/1975 | Woodruff | 426/312 |
| 3,943,987 | 3/1976 | Rossi | 150/0.5 |
| 3,980,226 | 9/1976 | Franz | 229/62.5 |
| 4,055,672 | 10/1977 | Hirsch et al. | 426/127 |
| 4,066,401 | 1/1978 | Solomon | 21/61 |
| 4,122,197 | 10/1978 | Krugmann | 426/232 |
| 4,184,310 | 1/1980 | Shelby | 426/396 |
| 4,424,659 | 1/1984 | Perigo et al. | 53/425 |
| 4,427,705 | 1/1984 | Wyslotsky et al. | 426/129 |
| 4,513,015 | 4/1985 | Clough | 426/396 |
| 4,548,824 | 10/1985 | Mitchell et al. | 426/396 |
| 4,548,852 | 10/1985 | Mitchell | 426/396 |
| 4,627,336 | 12/1986 | Nam | 426/418 |
| 4,642,239 | 2/1987 | Ferrar et al. | 426/129 |
| 4,685,274 | 8/1987 | Garwood | 53/433 |

FOREIGN PATENT DOCUMENTS

| | | |
|---|---|---|
| 843886 | 6/1970 | Canada. |
| 2244601 | 3/1974 | Fed. Rep. of Germany. |
| 2351008 | 1/1978 | France. |
| 581098 | 8/1958 | Italy. |
| 1186978 | 4/1970 | United Kingdom. |

OTHER PUBLICATIONS

*Integrated Total System Modified Atmosphere Packaging for Retail Red Meat Cuts*, pp. 121-139 John Sumner, Tony Garwood, Royal Melbourne Institute of Technology, Melbourne Australia, Cap '86.
Multivac R 5100, Koch Multivac.
Notil Provisioner 1/31/59.

*Primary Examiner*—Steven Weinstein

[57] ABSTRACT

A method and apparatus for packaging perishable products is disclosed, said method and apparatus enabling the alteration of the gaseous environment surrounding a given product. The packaging system can be readily prepared for immediate transport and aging, retail display and consumer freezing. The present system comprises a relatively rigid tray which is sealed with a flexible gas impermeable cover, said tray being provided with a resealable septum valve. The tray is also preferably provided with a plurality of protrusions or mounds so as to facilitate gas flow and contact with a given perishable product. The atmosphere in the packaging system may be modified to inhibit bacterial decay of the product and/or to enhance its appearance. Likewise, the package may be prepared for freezing by drawing a substantial vacuum within the packaging system.

12 Claims, 2 Drawing Sheets

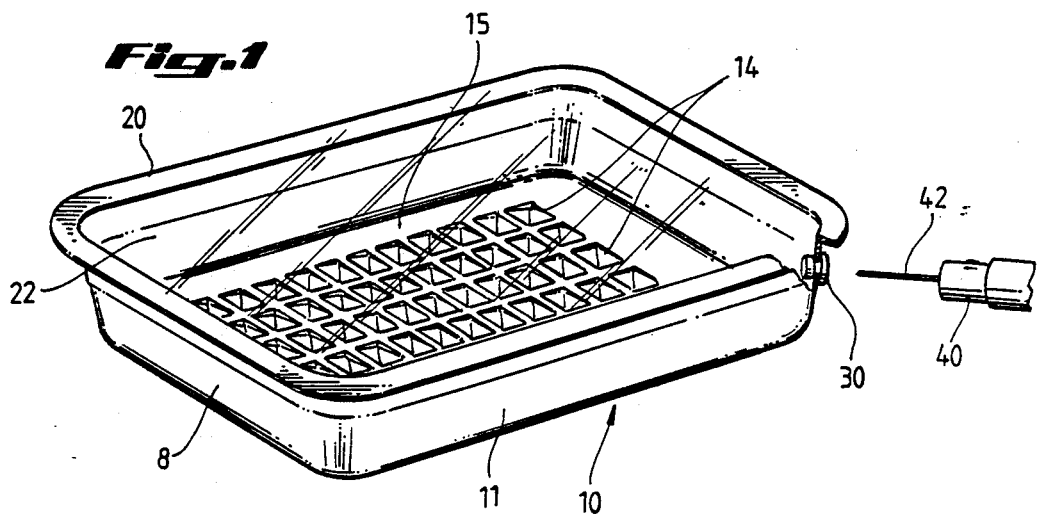
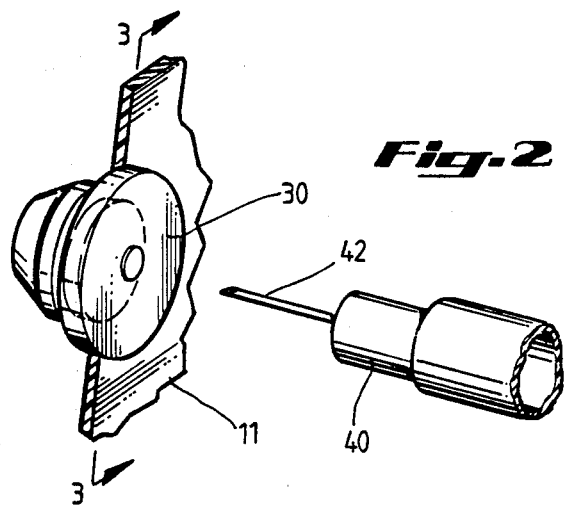
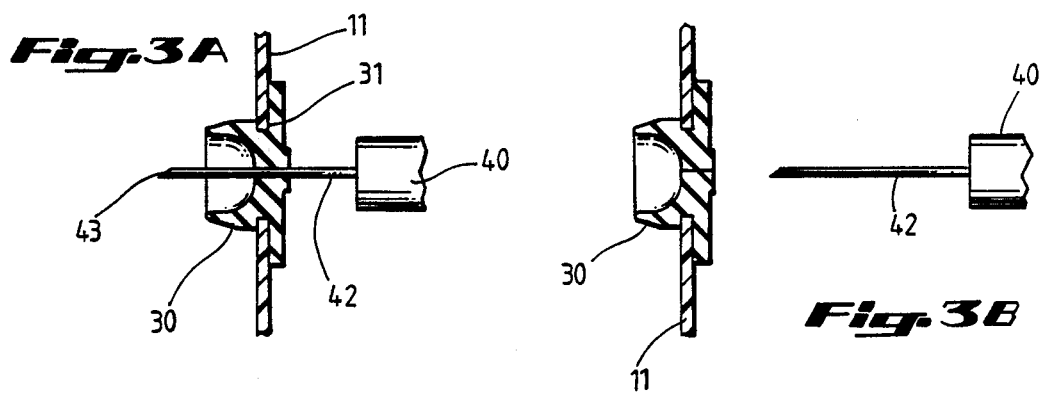

METHOD FOR PACKAGING PERISHABLE PRODUCTS

This is a divisional of application Ser. No. 094,384, filed Sept. 8, 1987 now abandoned.

BACKGROUND OF THE INVENTION

1. Field of the Invention

The present invention relates to the packaging of perishable products, particularly shelf products such as meats, which are transported from an original packaging facility to a local retail outlet for purchase by the consumer with the prospect of home freezing.

2. Description of the Prior Art

Perishable products, especially meats, are generally cut and packaged at a slaughterhouse or other processing facility preparatory to shipment to various retail outlets. These meat products are commonly packaged in the normal oxygen-nitrogen atmosphere naturally occurring in such processing facilities. Exposure and packaging of perishable products in an ordinary oxygen-nitrogen atmosphere, however, eventually results in spoilage, both from bacterial decay, and in the case of red meat, from the conversion of myoglobin meat pigment to the grey or brown metmyoglobin, which color change renders the meat unacceptable to the average consumer. However, if air circulation around the product is limited or excluded, other generally undesired anaerobic phenomenon occurs, and meat loses its red color. This is because exposure to oxygen at temperatures above freezing is desirable for meat in order to oxygenate the meat pigment to bright red oxymyoglobin. The presence of this red oxymyoglobin produces the red "bloom" which is often desired by the consumer of such meat products.

Fresh meat is considered more desirable by many consumers if it is allowed to age for a period of days. It is known that an acceptable method of aging fresh meat is by vacuum packaging. Another acceptable method of aging fresh meat is packaging in an inert gas atmosphere such as a nitrogen gas atmosphere.

It is also known in the art to package perishable products in an atmosphere which inhibits bacterial growth, such as carbon dioxide.

It is also known in the art to vacuum package perishable products in order to extend their overall shelf life.

It is also known in the art that bacterial growth may be inhibited by packaging red meat in an atmosphere containing enriched oxygen and carbon dioxide. Alternatively, it is known in the art that the formation of oxymyoglobin over metmyoglobin may be achieved by packaging red meat in an atmosphere of pure or enriched oxygen.

Packaging may thus be designed to encourage maximum exposure of the surface of the packaged product to a modified atmosphere, thus significantly extending the shelf-life of the product and reducing wastage through spoilage, both of which are advantages to the retailer. Packaging may also be designed to encourage maximum exposure of the packaged product to a second atmosphere so as to enhance its aesthetic appeal and thus its marketability to the consumer.

An example of a package designed to take advantage of these known principles is seen in U.S. Pat. No. 4,055,672. In this patent, a perishable meat product is wrapped with a gas permeable membrane and is then sealed in a gas impermeable package while in the presence of an inert atmosphere. When display of the product is desired, the impermeable cover of the package is removed, thus allowing oxygen to reach the meat product, thereby producing the red "bloom" desired by consumers of such products.

Disadvantages associated with this package design include its inability to enable the retailer to retard or slow the deterioration of the fresh product once the impermeable cover is removed from the package. When the internal wrapped contents are exposed to a normal oxygen-nitrogen atmosphere, the meat undergoes a declining state of freshness and normally enjoys a maximum shelf life of about three days. Thus, if a retailer incorrectly assesses the demand for a given meat product, the unsold product declines in freshness and must either be sold at a reduced price or thrown away.

It is increasingly common for the consumer to freeze perishable products bought fresh in supermarkets or similar outlets in order to extend their relative shelf life. When such products are frozen, however, exposure to air or other gaseous atmospheres causes discoloration through dehydration, or so called "freezer burn". This renders the food less attractive and adversely affects its quality. The packaging described above, which is designed to increase exposure to the atmosphere in the package, is therefore highly unsuitable for the purpose of freezing. If the consumer places such packaging in a home freezer, freezer burn almost inevitably results. In order to avoid freezer burn, the consumer often must completely repackage this product at home, which is time consuming and oftentimes inconvenient. The result of these disadvantages has been that this type of packaging, while it reduces waste and is otherwise advantageous to the retailer, has not found general consumer acceptance in applications where home freezing is desired.

Packaging designed to specifically address the problem of "freezer burn" normally involves vacuum packing the perishable product between two impermeable membranes which are then thermosealed to form an air tight unit. Disadvantages associated with this type of system include the generally increased cost and inconvenience associated with the packaging, exhibition and repackaging of the product prior to home freezing. If a meat product is vacuum packed at the original processing facility, the product retains a generally purplish color since no oxymyoglobin is formed due to a lack of oxygen. This color is sometimes unacceptable for domestic retail marketing, resulting in the product being removed from the vacuum packaging prior to display and repackaged in a method allowing a gas atmosphere with enough oxygen for "bloom" to occur. If a consumer then desires to subsequently freeze the product, the meat product must again be securely packaged in a fashion to minimize the presence of free gases, this repackaging process resulting in a duplication of effort, waste of materials, and higher production costs.

SUMMARY OF THE INVENTION

The present invention addresses the above-noted and other disadvantages by providing a simple, economical packaging system for perishable products, including food products, which may securely and interchangeably retain a variety of different atmospheres so as to enhance the transport and shelf-life of said products, while enhancing the aesthetic presentation quality of these products to the consumer. Further, the present packaging system is also capable of being readily prepared by the retailer for home freezing by the consumer so that dehydration and discoloration of the perishable product during freezing is greatly reduced. The present system also allows the retailer to maintain greater atmospheric control over a given product.

In a broad aspect, the present invention comprises a system for exchanging or otherwise modifying the atmosphere about a perishable food product for variable conditions. More particularly, the system is directed primarily at packaging for the retail market and comprises a substantially impermeable package or envelope equipped with a reusable, self-sealing port or passageway. A first portion of the package is preferably sufficiently rigid to support the perishable product, and a second portion comprises a flexible film or other layer capable of being inflated or being shrunk to fit against the product. The interior of the package is preferably configured to expose substantially the entire surface of the product, or as much of the entire surface as practicable, to the atmosphere within the package. Any portion of the package, normally the film portion, is also preferably transparent to permit viewing of the product.

The package of the invention, as noted above, preferably comprises two portions which are at least initially separate or separable to receive the product to be packaged. After the product is placed within the package, the two portions are joined and sealed and then processed to provide an appropriate atmosphere within the package. Once the package is joined and sealed, access to the interior is preferably attained by inserting a hollow needle or the like through the self-sealing septum valve.

According to a preferred form of the invention, the present packaging system includes a relatively rigid bottom tray which is secured by a flexible cover so as to form a substantially gas impermeable unit. This bottom tray is provided with a self-sealing septum valve to allow for the introduction or modification of a given atmosphere into the unit subsequent to packaging. The self-sealing septum valve is generally comprised of a passageway which is blocked by a wall capable of being penetrated by a hollow needle or the like, and further capable of sealing itself upon removal of the needle. In effect, such a valve is open when a sufficiently slender probe, needle or other conduit is inserted through its septum. The valve closes upon removal of the conduit.

In one preferred embodiment, a septum valve may be provided in one corner of the bottom tray such as to allow for the injection and/or withdrawal of various and desired atmospheres. Placement of the septum valve in this fashion does not impair the stackability of the package, and further serves to protect the valve from inadvertent penetration during packaging and transport.

In this embodiment, the gaseous atmosphere contained in the space between the tray and cover may be comprised of a composition of gases, preferably inert gases, suitable for the preservation of a particular perishable product placed in the package. In the case of red meat, this composition preferably consists essentially of nitrogen or a mixture of nitrogen and carbon dioxide.

Alternatively and/or sequentially, the nitrogen or nitrogen and carbon dioxide atmosphere previously described for the preservation of the perishable product may be modified or replaced with an atmosphere having a substantially higher oxygen concentration than that present in the normal atmosphere. This replacement atmosphere may be desirable in order to encourage the formation of oxymyoglobin in meat products, thus enhancing the aesthetic appeal and hence the marketability of the product. This alternate atmosphere is preferably introduced into the package via the self-sealing septum valve disposed in the rigid tray. The same valve may also be used to evacuate the former atmosphere and any associated and undesired moisture that may accumulate in the tray after packaging.

If freezing of the product is desired subsequent to purchase, the atmosphere present in the packaging system may again be modified to decrease or substantially eliminate "freezer burn". Preparation for freezing in this manner may be accomplished by evacuating the gases present within the container so as to create a substantial vacuum between the rigid tray and the cover. These gases may be evacuated through the septum valve previously described. This final preparation may be performed at the retail outlet, and normally involves the placement of the package in a special apparatus whereby an atmosphere exchange device is inserted through the septum valve to draw a vacuum on the interior of the package.

The described method and apparatus for packaging a perishable product, such as fresh meat, enables the product to travel, in a single package system, from the original processor of the product to the consumer's freezer. The package preferably includes valving that enables gases to be inserted or withdrawn from the package without a loss of system integrity. While the described packaging system is preferably rigid to facilitate stacking and to withstand the differential pressures of vacuum packaging, the system also advantageously maintains sufficient flexibility to accommodate a variety of internal pressures.

Such a packaging system is therefore capable of enabling "aging", "coloring" and freezing in succession, with a minimum of inconvenience. An anaerobic or other favorable atmosphere such as a vacuum may thus be established at the producer or processor so that the product ages enroute to the distributor. The distributor may then color the product by injecting the necessary oxygen and/or oxygen and carbon dioxide environment. Finally, a vacuum may be drawn within the package to ready the product for freezing.

While it is anticipated that the claimed invention may have significant utility for perishable meat products, it is also envisioned that the present system may have additional uses in the medical or chemical industries where it is desirable to maintain or modify a given atmosphere. Such uses may include equipment sterilization systems or systems where controlled, atmospherically induced reactions are desired.

Accordingly, it is a general advantage of the present invention that it provides a package for perishable products, notably food products, which prolongs the shelf life of these products, enhances the aesthetic appeal of the products to the consumer, and which ultimately reduces dehydration and discoloration of the products during freezing. It is a further advantage of this invention to provide a packaging method and structure which permits a product to travel from the producer to the consumer in a single receptacle whose atmosphere may be varied to accomplish aging, coloring and preserving in succession.

Other objects and advantages of the invention will become apparent from the following detailed description made in conjunction with the accompanying drawings.

BRIEF DESCRIPTION OF THE DRAWINGS

FIG. 1 illustrates a perspective view of a packaging system embodying the features of the present invention.

FIG. 2 illustrates a perspective cutaway view showing the septum valve as it may be situated in the tray wall.

FIGS. 3A and 3B illustrate a cutaway, partially sectioned side view of the valving of the present invention as taken through plane 3—3 of FIG. 2.

DETAILED DESCRIPTION OF THE DRAWINGS

Figure 4:
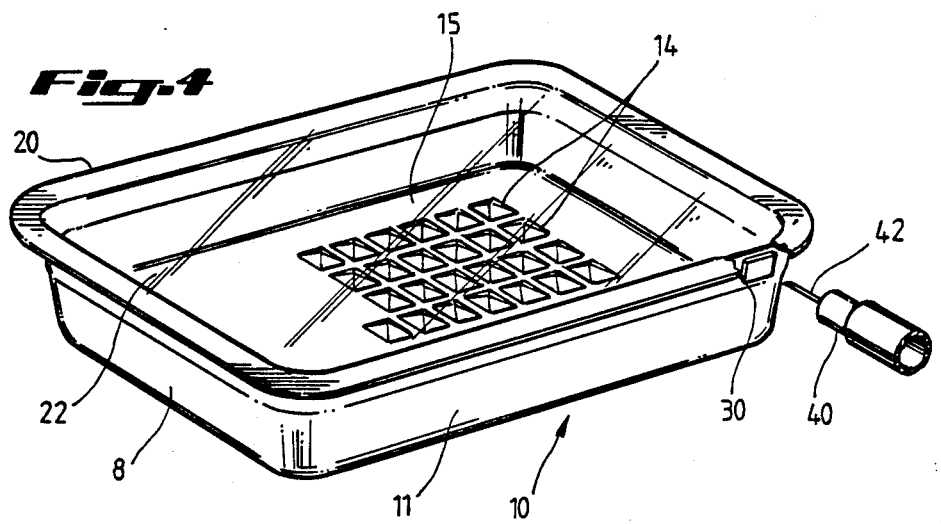
Figure 5:
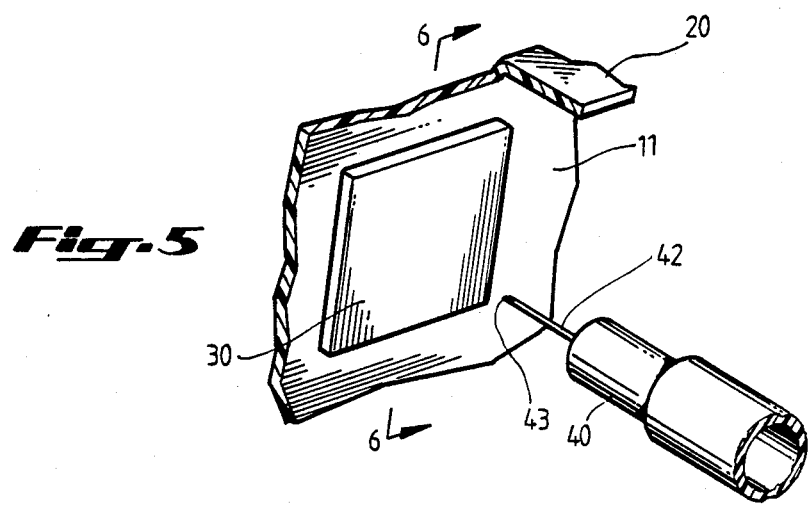
Figure 6A:
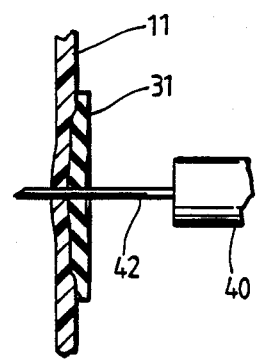
Figure 6B:
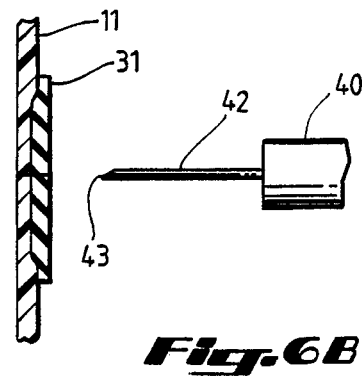

The packaging system 10 illustrated in FIG. 1 is preferably made of a relatively rigid plastic bottom tray 8 which is secured by a flexible cover 22 so as to form an airtight package. Preferably, the cover 22 is made of a transparent, high oxygen barrier film which is substantially gas and liquid impermeable. While the packaging system 10 may assume a variety of configurations, it is illustrated in a thermoformed rectangular configuration.

Preferably, the interior surface of the bottom of the tray 8 is provided with a series of closely spaced mounds 14. These mounds may be approximately conical in shape, but they may also be in the form of pyramids or other shapes sufficient to accomplish the noted purpose. These mounds 14 support a perishable product placed in the tray above the bottom surface of the tray, thus allowing gaseous circulation over most of the lower surface of the product. A means for absorbing liquid exudates, such as an absorbent mat (not shown) may be placed beneath the perishable product.

The side surfaces 11 of the lower tray 8 may define a peripheral flange 20 at their upper extent. In this fashion, once the perishable product has been located within the tray 8, the flexible, gas impermeable sheet or cover 22 may be sealed to the flange 20 by adhesive or thermobonding techniques. The side surfaces 11 advantageously have a height slightly greater than the thickness of the perishable product.

As may be seen by reference to FIGS. 1 and 2, a septum valve 30 is preferably disposed in a corner of the bottom tray 8 such that the atmosphere contained between the tray 8 and the cover 22 may be modified or withdrawn upon insertion of an atmosphere exchange device 40. This septum valve 30 may be affixed to the tray 8 by conventional bonding techniques such as thermobonding or adhesive bonding, so as to effect a gas and water tight fit. The septum valve itself 30 is preferably composed of a resilient rubber-like compound which is self-sealing when used with an atmosphere exchange device 40. An example of such a valve 30 might be a U-24 stopper valve manufactured by the West Company of Phoenixville, Pa.

A packaging system as described above is prepared for transport from the producer to the retail outlet in the following fashion. The producer or processor may initially load the product into the tray 8 and close the packaging system 10 with the cover 22. When a meat product is involved, an anaerobic environment may be established within the packaging systems by performing the above steps in the presence of a nitrogen or nitrogen rich atmosphere. Alternatively, an anaerobic environment may be established within the system 10 by exhausting the air or other non-inert gas through the septum valve 30 via an atmosphere exchange device 40 inserted in the package subsequent to sealing the cover 22 on the base 8. In some applications, a substantial vacuum may be desired. Alternatively, the system 10 may be filled via the septum valve 30 with an inert gas. This inert gas is preferably composed of nitrogen, or a mixture of nitrogen and carbon dioxide, and may be pumped into the system 10 through the atmosphere exchange device 40. In either case, the product "ages" in route between the producer and the distributor in an anaerobic environment.

The above described packaging system 10 may be employed for many different purposes. A typical purpose might be to prepare for retail display and sale of a red meat product assuming that the product has previously been packaged in an anerobic atmosphere. In accordance with the invention, the package system 10 is first placed in a special processing apparatus and the insertion portion 42 of an atmosphere exchange device 40 is inserted through the septum valve 30 disposed in the tray wall 11. Preferably, the atmosphere exchange device 40 is inserted only so far as to fully pierce the valve 30 and not so far as to contact the food product within the system 10. The inert atmosphere as well as any undesired fluids are drawn out of the packaging system 10 through the device 40 until a substantial vacuum is established. Then a new gas mixture is injected. In the case of red meat, this gaseous mixture preferably contains oxygen and carbon dioxide in suitable compositions, with a preferred composition of the gaseous mixture being approximately 80% oxygen, and 20% carbon dioxide. In this way, the red "bloom" may be created in the aged meat product.

It is also envisioned that the present system 10 may be utilized where a perishable product is packaged at the retail outlet. In such a case, a food product, such as a bakery or a raw fruit or vegetable, is placed in a tray 8 of suitable size and the cover 22 is secured. The system 10 may contain ordinary air, but in the preferred embodiment after the cover 22 is applied and sealed, the air within the system 10 is flushed out or extracted and replaced by a suitable gaseous mixture via an atmosphere exchange device 40. Suitable labeling may then be applied to the outside of the packaging by separate labels affixed to the package or by printing on the cover itself.

The atmosphere within the package 10 may be altered by connecting the septum valve 30 to a source of gas under pressure. The gas within the package 10 may be purged by extracting the old atmosphere through the septum valve 30 and then inletting the replacement gas in the same manner.

FIGS. 3A and 3B illustrate a cross sectional illustration of the septum valve 30 as it may be situated in a wall 11 of the present system 10. As may be seen, the valve 30 is preferably provided with a retaining groove 31 so as to maintain the posture of the valve 30 in relation to the wall 11 during insertion and withdrawal of the insertion portion 42 of the atmosphere exchange device 40. To introduce or modify a given atmosphere, the hollow insertion portion 42 of the atmosphere exchange device 40 is inserted into the container through the septum valve such that the open terminal end 43 of the device 40 extends within the container. After a given atmosphere is introduced, the insertion portion 42 of the atmosphere exchange device 40 is withdrawn from the container through the valve. The structure of the valve 30 is such that upon the removal of the exchange device 40, the valve 30 again forms an air tight seal in the container by resiliently expanding to close the hole formed in the valve 30 by the device 40.

While certain specific and preferred embodiments of the present invention have been illustrated herein, it will be understood that still further variations and modifications can be made therein without departing from the spirit and scope of the invention as claimed below.

What is claimed is:

1. A method for processing a perishable fresh meat product for controlled aging and subsequent presentation to the consumer, comprising the sequential steps of:
   positioning the product on a gas impermeable package tray;
   sealing said product on said tray in a non-inert atmosphere with a gas impermeable cover so as to form a gas tight package;
   inserting an atmosphere exchange apparatus through a septum valve disposed in the tray
   removing the non-inert gas from within the package through said valve disposed in said package;
   filling the interior of the package through said valve with a first gas capable of forming an anaerobic atmosphere in said package;
   aging said product in the anaerobic atmosphere in said package;
   removing said first gas from said package though said valve;
   filing the interior of said package with a second gas conducive to the formation of oxymyoglobin in said meat product;
   maintaining said meat product in said package in said second gas for at least a time sufficient to product a bloom in said meat product;
   removing said second gas from the package through said valve; and
   freezing said product while in said package.

2. The method of claim 1 wherein the first gas is inert.

3. The method of claim 2 wherein the inert gas consists essentially of nitrogen.

4. The method of claim 2 wherein the inert gas comprises a mixture of nitrogen and carbon dioxide.

5. The method of claim 1 wherein the atmosphere conducive to the formation of oxymyoglobin comprises a mixture of oxygen and carbon dioxide.

6. The method of claim 5 wherein the oxygen - carbon dioxide atmosphere is comprised of a ratio of approximately 80% oxygen and 20 % carbon dioxide.

7. A method for packaging a perishable fresh meat product for controlled aging and subsequent presentation to the consumer, comprising the sequential steps of:
   positioning said product on a substantially impermeable package tray while in an anaerobic, inert gas atmosphere;
   sealing said product on said tray in said anaerobic inert gas atmosphere with a substantially gas impermeable cover so as to form a gas tight package;
   aging said product in said anaerobic inert gas atmosphere;
   inserting an atmosphere exchange apparatus through a septum valve disposed in said tray
   removing said inert gas from said package through said valve;
   filling through said valve the interior of said package with a second atmosphere conducive to the formation of oxymyoglobin in said meat product; and
   maintaining said meat product in said package in the second atmosphere for at least a time sufficient to produce a bloom in said product, 8. The method of claim 7 wherein the inert gas consists essentially of nitrogen.

9. The method of claim 7 wherein the inert gas comprises essentially a mixture of nitrogen and carbon dioxide.

10. The method of claim 7 wherein the atmosphere conducive to the formation of oxymyoglobin comprises a mixture of oxygen and carbon dioxide.

11. The method of claim 10 wherein the oxygen - carbon dioxide atmosphere comprises a ratio of approximately 80% oxygen and 20% carbon dioxide.

12. The method of claim 37 further comprising the sequential steps of: removing the second atmosphere from the package through the valve; and freezing the fresh meat product while in the package.

* * * * *

UNITED STATES PATENT AND TRADEMARK OFFICE
CERTIFICATE OF CORRECTION

PATENT NO. : 4,919,955
DATED : April 24, 1990
INVENTOR(S) : Jerry L. Mitchell

It is certified that error appears in the above-indentified patent and that said Letters Patent is hereby corrected as shown below:

Col. 7, line 27, replace the word "though" with -- through --.

Col. 7, line 34, please replace the word "product" with -- produce --.

Col. 8, line 39, please delete "37" and insert -- 7 --.

Signed and Sealed this

Second Day of August, 1994

BRUCE LEHMAN

*Attest:*

*Attesting Officer*     Commissioner of Patents and Trademarks